United States Patent [19]

Gao

[11] Patent Number: 5,189,200

[45] Date of Patent: Feb. 23, 1993

[54] PROCESS FOR THE STEREOSELECTIVE TRANSFORMATION OF A DIOL TO AN ALCOHOL

[75] Inventor: Yun Gao, Framingham, Mass.

[73] Assignee: Sepracor, Inc., Marlborough, Mass.

[21] Appl. No.: 631,808

[22] Filed: Dec. 21, 1990

[51] Int. Cl.$^5$ .................. C07C 69/675; C07C 69/70
[52] U.S. Cl. ............................. 560/180; 549/34;
560/151; 562/581; 562/582; 564/160
[58] Field of Search ............... 562/581, 582; 560/180,
560/151; 549/34; 564/160

[56] References Cited

U.S. PATENT DOCUMENTS 4,960,904 10/1990 LeRoy et al. .................... 549/34
5,023,342 6/1991 Sharpless et al. ................. 549/34

OTHER PUBLICATIONS

Pizey, *Synthetic Reagents*, vol. 1, pp. 331–333, (J. Wiley, 1974).
Chibata et al., *Pure Appl. Chem.* 50: 667 (1978).
Wynberg et al., *J. Am. Chem. Soc.* 104: 166 (1982).
Henrot et al., *Synth. Commun.* 16: 183 (1986).
Hungerbühler et al., *Angew. Chem. Int. Ed. Engl.* 18: 958 (1979).
Alpegiani et al., *J. Org. Chem.* 52: 278 (1987).
Gao et al., *J. Am. Chem. Soc.* 110: 7538 (1988).
Kusuda et al., *Tetrahedron Lett.* 30: 2945 (1989).
*Beilsteins HandBuch der Organischen Chemie*, Band III, 417–420.
Schiller, E., *Berichte* 42: 2017 (1909).
Stinson, S., *Chemical & Engineering News*, p. 22, Oct. 31, 1988.

*Primary Examiner*—José G. Dees
*Assistant Examiner*—B. Frazier
*Attorney, Agent, or Firm*—Pennie & Edmonds

[57] ABSTRACT

An efficient and commerically-viable method for the stereoselective transformation of a diol to an alcohol is disclosed. The present method is particularly well-suited for the preparation of the unnatural D-isomer of malic acid or its derivatives from the abundant naturally occurring L-tartaric acid or derivatives thereof.

5 Claims, No Drawings

PROCESS FOR THE STEREOSELECTIVE TRANSFORMATION OF A DIOL TO AN ALCOHOL

TABLE OF CONTENTS

1. Field of the Invention
2. Background of the invention
   2.1 Stereochemistry
   2.2 Previous Methods for the Preparation of Malic Acid
3. Summary of the Invention
4. Nomenclature
5. Detailed Description of the Invention
   5.1 Preferred Embodiments
   5.2 Examples
   5.3 General Experimental Conditions
   5.4 Preparation of D-(+)-diisopropyl malate
   5.5 Preparation of D-(+)-diisopropyl malate
   5.6 Preparation methyl 2-ethyl-3-methyl-3-hydroxypropionate
   5.7 Preparation of D-(+)-diisopropyl malate
   5.8 Preparation of methyl 3-hydroxy-3isopropyl propionate
   5.9 Preparation of D-(+)-diisopropyl malate from L-(+)-diisopropyl tartrate
   5.10 Preparation of methyl 2-methyl-3-ethyl-3-hydroxypropionate
   5.11 Preparation of D-(+)-diethyl malate
   5.12 Preparation of D-(+)-N,N,N',N'-tetraethyl malamide from L-(+)-N,N,N'-tetraethyl tartramide
   5.13 Preparation of D-(+)-diethyl malate from L-(+)-diethyl tartrate
   5.14 Preparation of D-(+)-diethyl malate
   5.15 Preparation of D-(+)-diphenyl malate from L-(+)-diphenyl tartrate
   5.16 Preparation of D-(+)-diethyl malate
   5.17 Preparation of D-(+)-diethyl malate
   5.18 Preparation of D-(+)-dimethyl malate from L-(+)-dimethyl tartrate
   5.19 Preparation of D-(+)-diisopropyl malate

1. FIELD OF THE INVENTION

The present invention relates to a method for the stereoselective transformation of a diol into an alcohol via a cyclic sulfite moiety. In particular, the present invention relates to the formation of a cyclic sulfite moiety from a 1,2- or 1,3-diol, the ring-opening displacement of the cyclic sulfite by a suitable nucleophile and the subsequent removal of the attached nucleophile under reducing conditions. The present invention is stereoselective in that any optical activity present in the initial diol substrate is preserved in the product alcohol.

The disclosed method is particularly suitable for the preparation of the D- or L-isomers of malic acid.

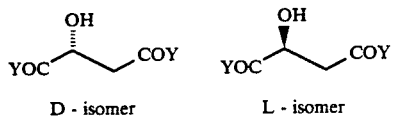

2. BACKGROUND OF THE INVENTION

2.1. Stereochemistry

The study of the spatial arrangement of atoms in a compound and their relation to the properties of the compound is called stereochemistry. Stereoisomers are molecules which possess identical chemical formulas with the same atoms bonded to one another, however they differ in the manner in which these atoms are arranged in three dimensional space. Optical isomers or enantiomers are molecules that are mirror images but are nonetheless nonsuperimposable. Such molecules can rotate the plane of plane-polarized light. Molecules that exhibit this phenomenon are said to be optically active. In describing an optically active compound, the prefixes D and L or R and S are used to denote the absolute configuration of the molecule about its chiral center(s). A chiral center is usually an asymmetric carbon atom, that is, one with four different groups attached to it. The prefixes (+) and (−) or d and l are employed to designate the sign of rotation of plane-polarized light by the compound. A compound with the prefix (-) or l is levorotatory. A levorotatory compound rotates plane-polarized light to the left (counterclockwise). A compound prefixed with (+) or d is dextrorotatory. A dextrorotatory compound rotates plane polarized light to the right (clockwise). As mentioned above, a specific stereoisomer may also be referred to as an enantiomer, and a mixture of such isomers is often called an enantiomeric or racemic mixture.

The property of optical activity is due to molecular asymmetry about carbon atoms that are linked to four different atoms. Where there is only one asymmetric carbon atom, or chiral center as it is sometimes called, there are two possible stereoisomers. Where there are n asymmetric carbons or chiral centers, the number of potential stereoisomers increases to $2^n$. Thus, a molecule with three chiral centers would have eight possible stereoisomers.

While the structural differences between stereoisomers are subtle and of little consequence in ordinary chemical reactions, they may be profound where biological systems are concerned, i.e., if the compounds are utilized in enzyme-catalyzed reactions. Thus, the L-amino acids are metabolized in humans but the corresponding D-analogs are not, and only D-glucose can be phosphorylated and processed into glycogen or degraded by the glycolytic and oxidative pathways or intermediary metabolism. Similarly, beta blockers, pheromones, prostaglandins, steroids, flavoring and fragrance agents, pharmaceuticals, pesticides, herbicides and many other compounds exhibit critical stereospecificity. In the field of pesticides, Tessier (*Chemistry and Industry, 1984*, March 19, 199) has shown that only two of the eight stereoisomers of deltamethrin, a pyrethroid insecticide, have any biological activity. The same statement concerning the concentration of bioactivity in a single isomer can be made about many other pesticides, including the phenoxypropionates and halopropionate derivatives, each containing one chiral center and existing in the form of two optical isomers.

Stereochemical purity is of equal importance in the field of pharmaceuticals, where 12 of the 20 most prescribed drugs exhibit chirality. A case in point is provided by naproxen, or (+)-S-2-(6-methoxy-2-naphthyl)-propanoic acid, which is one of the two most important members of a class of 2-arylpropanoic acids with nonsteroidal anti-inflammatory activity used, for instance, in the management of arthritis. In this case, the S(+) enantiomer of the drug is known to be 28 times more therapeutically potent than its R(−) counterpart. Still another example of chiral pharmaceuticals is provided by the family of beta-blockers; the L-form of propranolol is known to be 100 times more potent than the D-enantiomer.

Synthesis of compounds with asymmetric centers by standard organic synthetic techniques generally leads to a racemic mixture which, in the aggregate, may have a relatively low specific bioactivity since certain of the stereoisomers in the mixture are likely to be biologically or functionally inactive. As a result, larger quantities of the material must be used to obtain an effective dose, and manufacturing costs are increased due to the co-production of stereochemically "incorrect" and hence, inactive ingredients.

Thus, optical purity or enantiomeric excess is a very important consideration in the design of chemical syntheses of optically active compounds.

2.2. Previous Methods for the Preparation of Malic Acid

Malic acid is an extremely valuable chiral starting material for synthesis of chiral complex natural products, agrochemicals and pharmaceuticals.

While the natural L-(−)- or R-malic acid, also known as apple acid, is readily available, the unnatural D-(+)- or S-isomer is more difficult to obtain. Due to its usefulness, extensive efforts have been directed to the preparation of optically pure malic acid and its derivatives. Several methods including enzymatic processes, catalytic asymmetric synthesis and asymmetric transformations of readily available chiral natural products have been developed.

For example, Chibata et al., (*Pure and Appl. Chem.* 978, 50, 667) have utilized fumaric acid and immobilized fumarase to obtain a mixture of products containing 80% of the natural L-malic acid. However, this method cannot furnish the unnatural D-isomer due to the stereospecificity of the enzyme. Wynberg et al., (*J. Am. Chem. Soc.* 1982, 104, 166) have developed an asymmetric synthesis of D- and L-malic acid using chiral alkaloid-catalyzed cyclization of ketene and chloral, followed by stereoselective hydrolysis of the cyclized product. For example, L-malic acid can be obtained in three steps in 79% yield and 98% enantiomeric excess (ee) using quinidine as the catalyst. However, the unnatural D-malic acid can only be prepared in 76% ee using quinine as the catalyst.

Another strategy for the preparation of optically pure malic acid and its derivatives involves stereoselective transformations of readily available, inexpensive chiral natural products such as α-amino acid and optically pure tartaric acid and its derivatives. For example, Henrot et al., (*Synth. Commun.* 1986, 16, 183) are able to prepare L- and D-malic acid from L- and D-aspartic acid, respectively, in three steps and 68% yield. However, the synthesis of D-malic acid involves the use of less accessible and expensive D-aspartic acid.

Because of its abundance, tartaric acid, especially the natural L-isomer, has been widely used for the preparation of optically pure malic acid and its derivatives. From the naturally-occurring L-tartaric acid, the unnatural D-malic acid is produced. For examples, Hungerbühler et al., (*Angew. Chem. Int. Ed. Engl.* 1979, 18, 958) prepared D-dimethyl malate from L-dimethyl tartrate via the reduction of the corresponding β-bromo malate by tributyltin hydride in four steps and 44% yield. Alpegiani et al., (*J. Org. Chem.* 1987, 52, 278) obtained D-dimethyl malate from L-dimethyl tartrate via the reduction of the corresponding thionocarbonate derivative by tributyltin hydride in two steps and 67% yield. Gao et al., (*J. Am. Chem. Soc.* 1988, 110, 7538) have developed a general method for the preparation of D-malate from L-tartrate via the reduction of the corresponding tartrate cyclic sulfate by sodium cyanoborohydride. For example, D-diisopropyl malate is prepared in 50% overall yield from L-diisopropyl tartrate. More recently Kusuda et al., (*Tetrahedron Lett.* 1989, 30, 2945) prepared D-diisopropyl malate from L-(+)-diisopropyl tartrate directly by the reduction of the latter with samarium iodide in 99% yield. However, methods described above involve the use of expensive and hazardous reagents for the preparation of the intermediates and in subsequent reductions. Therefore, they are not amenable to the large-scale production of optically pure malic acid and its derivatives.

3. SUMMARY OF THE INVENTION

The present invention is directed to a process of transforming a compound of the formula I to a compound of the formula II

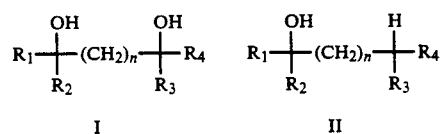

in which n=0 or 1, $R_1$, $R_2$, $R_3$ and $R_4$ represent independently a hydrogen atom, an aliphatic group, an aromatic group, an aromatic heterocyclic group, an aliphatic heterocyclic group or a carbonyl-containing group of the formula COY in which Y represents a hydrogen atom, a halogen atom, any of the groups recited previously for $R_1$−$R_4$ or a group of the formula $W(R_5)_m$ in which W represents a nitrogen atom, an oxygen atom or a sulfur atom and $R_5$ represents a hydrogen atom or any of the groups recited previously for $R_1$-$R_4$ provided that when W represents a nitrogen atom, m is equal to 2 and when W represents an oxygen atom or a sulfur atom, m is equal to 1 and $R_5$ may not be a hydrogen atom.

The principal steps of the process include: (a) allowing a compound of the formula I to react with a thionyl halide under conditions effective to form a cyclic sulfite; (b) allowing said cyclic sulfite to react with a suitable halide salt under conditions effective to form a halo-substituted acyclic sulfite; and (c) allowing said halide-substituted acyclic sulfite to react with a suitable reducing agent under conditions effective to provide a compound of the formula II.

In a particular embodiment of the present invention, a process is disclosed for the preparation of malic acid and its derivatives in which a tartaric acid derivative is transformed to the corresponding cyclic sulfite by reaction with a thionyl halide such as thionyl chloride or thionyl bromide. The resulting cyclic sulfite is then treated with an inorganic halide, followed by reduction of the resulting β-halo malic acid derivative with reducing metal or by noble-metal-catalyzed hydrogenation with hydrogen gas to give a malic acid derivative after workup. Malic acid is then obtained by a subsequent transformation of the malic acid derivative (e.g., by hydrolysis of the corresponding ester of malic acid). The intermediates can be isolated or more conveniently used without isolation, thus permitting the entire process to be performed in one reactor. The present invention can be more easily understood with reference to the general equation (exemplified by the preparation of D-malic acid derivative) shown below:

Equation 1:

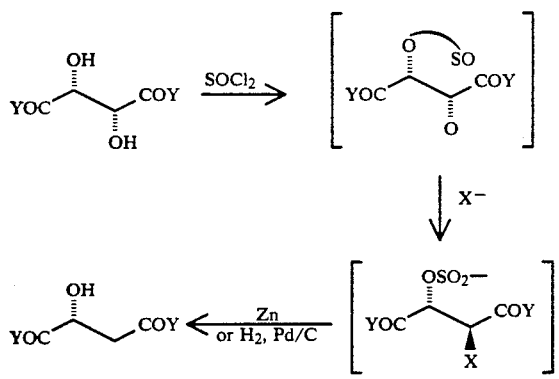

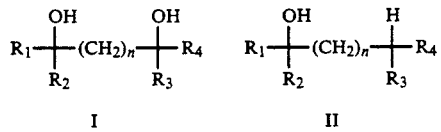

It is, therefore, an object of the present invention to provide a process for the stereoselective transformation of a diol to an alcohol.

It is, likewise, an object of the present invention to provide a practical process for the preparation of malic acid and its derivatives in high yield and high optical purity from L- or D-tartaric acid and its derivatives. In particular, the present invention contemplates the preparation of the unnatural D-malic acid and its derivatives from natural L-tartaric acid and its derivatives using inexpensive reagents and simple procedures.

It is a further object of this invention to provide a practical route to L- or D-malic acid where a malic acid derivative is prepared by a practical process followed by hydrolysis of said malic acid derivative to malic acid.

4. NOMENCLATURE

Unless otherwise indicated, the term aliphatic group encompasses linear, branched or cyclic hydrocarbons, including those that may possess a combination of such structural features. In addition, such hydrocarbons may also contain various substituents in which one or more hydrogen atoms has been replaced by functional group (that is, the aliphatic group may also be substituted). Thus, groups of chemicals such as alkanes, alkenes and alkynes fall within the meaning of this term.

Unless otherwise indicated, the term aromatic group means a hydrocarbon ring bearing a system of conjugated double bonds, usually comprising six or more even number of $\pi$ (pi) electrons, including those present as unshared pairs of electrons (i.e., lone pairs). Likewise, these aromatic groups may also be substituted with a variety of functional groups. Examples, of aromatic and substituted aromatic groups include, but are not limited to, phenyl, naphthyl, anisyl, toluyl, p-nitrophenyl and the like.

Aliphatic groups may also be substituted with aromatic groups (e.g., benzyl) and vice-versa (e.g., xylenyl). Heteroatoms, such as nitrogen, oxygen or sulfur, may also be present, particularly in cyclic structures, thus, giving rise to heterocycles, both aliphatic (e.g., tetrahydrofuranyl, tetrahydropyranyl, morpholino, piperidinyl, pyrrolidino and the like) and aromatic (e.g., imidazolino, furanyl, thienyl, thiazolyl, pyridinyl, pyrazinyl and the like).

5. DETAILED DISCUSSION OF THE INVENTION

In a general embodiment of the present invention, an efficient process for the replacement of one of two neighboring hydroxyl groups by hydrogen atom while retaining the stereochemistry of the diol substrate is disclosed. Thus, compounds of formula I, may be transformed readily and inexpensively to compounds of the formula II:

$$R_1 \underset{R_2}{\overset{OH}{\vert}} (CH_2)_n \underset{R_3}{\overset{OH}{\vert}} R_4 \qquad R_1 \underset{R_2}{\overset{OH}{\vert}} (CH_2)_n \underset{R_3}{\overset{H}{\vert}} R_4$$

I    II in which n=0 or 1, $R_1$, $R_2$, $R_3$ and $R_4$ represent independently a hydrogen atom, an aliphatic group, an aromatic group, an aromatic heterocyclic group, an aliphatic heterocyclic group or a carbonyl-containing group of the formula COY in which Y represents a hydrogen atom, a halogen atom, any of the groups recited previously for $R_1$-$R_4$ or a group of the formula $W(R_5)_m$ in which W represents a nitrogen atom, an oxygen atom or a sulfur atom and $R_5$ represents a hydrogen atom or any of the groups recited previously for $R_1$-$R_4$ provided that when W represents a nitrogen atom, m is equal to 2 and when W represents an oxygen atom or a sulfur atom, m is equal to 1 and $R_5$ may not be a hydrogen atom.

In one embodiment of the present invention, $R_1$ and $R_3$, $R_2$ and $R_4$, $R_1$ and $R_4$ or $R_2$ and $R_3$ of the diol of the formula (I) represent the same atom or group and are used as starting materials for the formulation of cyclic sulfite intermediates useful in the preparation of malic acid and its derivatives.

The cyclic sulfite is formed by the reaction of a compound of formula (I) with a thionyl halide such as thionyl chloride or bromide without solvent or in an inert solvent such as methylene chloride, ethyl acetate and dimethoxyethane (DME) at about 20°-100° C. in the presence of catalytic amount of N,N-dimethylformamide (DMF). The hydrogen halide formed during the reaction can be swept away with an inert gas and trapped with a basic solution or recycled. A stoichiometric amount of thionyl halide can be used. In practice, a slight excess (1.11-1.2 equivalents) of thionyl halide is used to ensure a complete reaction. The cyclic sulfite, which comprises a five-membered or a six-membered ring depending on the choice of compound I, can be isolated and purified if desired; however, it can be used directly, simply by removing the solvent.

The cyclic sulfite thus obtained is then treated with a suitable halide salt in a polar solvent at about 40°-100° C. in a separate or same reactor. The halides are inorganic halide salts, such as ammonium halide salts, alkali metal halide salts or alkaline-earth metal halide salts, for example, ammonium bromide, lithium bromide, lithium chloride, barium chloride, magnesium bromide, sodium iodide, sodium bromide, calcium chloride and the like. The suitable halide salt may also be an organic halide salt such as a tetra-alkyl substituted ammonium halide. A stoichiometric amount of halide salt is needed, but in practice 1.5-2.0 equivalents of halide salt are used to insure complete conversion. The resulting $\beta$-halo acyclic sulfite derivatives can be isolated, but more conveniently they are used without isolation.

Reduction of the β-halo acyclic sulfite derivatives, produced upon reaction of the cyclic sulfites with halide salt, may be performed either by treatment with finely divided active metal such as zinc, iron and tin or by catalytic hydrogenation in the presence of noble metals. For instance, reduction can be carried out with hydrogen in the presence of catalytic amounts of palladium on carbon or Raney nickel. After the β-halo acyclic sulfite is completely consumed, the desired compound of formula II can be obtained by filtration and extractive workup.

5.1. Preferred Embodiment

In a preferred embodiment of the present invention, dialkyl, or diaryl esters or amides of L- or D-tartaric acid are used as the starting materials for the formation of cyclic sulfite intermediates useful in the preparation of malic acid and its derivatives. Examples of esters include dimethyl, diethyl, and diisopropyl tartrates, which can be made by reaction of tartaric acid with the corresponding alcohol in the presence of an acid catalyst (e.g., $H_2SO_4$ or HCl). Other dialkyl esters or diaryl esters may be prepared likewise.

The cyclic sulfite is formed by the reaction of a tartrate or tartramide with a thionyl halide such as thionyl chloride or bromide without solvent or in an inert solvent such as methylene chloride, ethyl acetate and dimethoxyethane at 20°-100° C. in the presence of catalytic amount of N,N-dimethylformamide (DMF). The hydrogen halide formed during the reaction is swept away with an inert gas and trapped with a basic solution or recycled. A stoichiometric amount of thionyl halide can be used. In practice, a slight excess (1.1-1.2 equivalents) of thionyl halide is used to ensure a complete reaction. The reaction is normally complete in less than 10 hours. After the reaction, the excess thionyl halide is removed by distillation if isolation of the resulting cyclic sulfite is desired; this is done by distillation under vacuum. More conveniently the cyclic sulfite can be used directly, simply by removing the solvent without isolation and further purification. In some cases the solvent is used for the next reaction without removal.

The cyclic sulfite thus obtained is then treated with a suitable halide salt in a polar solvent (preferrably a polar aprotic one) at 20°-100° C. in a separate or the same reactor according to Equation 1. The halides are either organic halide salts such as ammonium or tetra-alkylammonium halide or inorganic halide salts such as alkali metal or alkaline-earth metal salts, for example, lithium bromide, lithium chloride, magnesium bromide, calcium chloride, sodium iodide and the like. A stoichiometric amount of halide is needed, but in practice 1.5-2.0 equivalents of halide are used to ensure complete conversion. Useful solvents include acetone, tetrahydrofuran (THF), dimethylformamide (DMF) and dimethoxyethane (DME) and the like. The concentration of the solution is about 0.5 M and above. The reaction can be monitored by thin layer chromatography on silica gel and is usually complete in less than 12 hours.

The resulting β-halo malic acid derivatives can be isolated, but more conveniently they are used without isolation. The β-halo malic acid derivatives are known and can also be obtained from a different route involving the reaction of tartaric acid derivatives such as dialkyl tartrate with phosphorus pentachloride or phosphorus tribromide (*Beilsteins Handbuch der Organischen Chemie*, Band III, 419).

Reduction of the β-halo malic acid derivatives produced upon the reaction of the cyclic sulfites with halide is performed either by an active metal such as zinc, iron, and tin or by catalytic hydrogenation with noble metals such as palladium, Raney nickel and the like. For example, after the cyclic sulfite is completely consumed, zinc dust, pre-washed with dilute hydrochloric acid, is added. If the cyclic sulfite is formed in situ from tartrate, a catalytic amount of water is added to the reaction mixture after the addition of zinc. If the cyclic sulfite is first isolated for use as the starting material, water is used as a co-solvent in an amount equal to that of the organic solvent. The reaction mixture is kept at the same temperature as the ring opening step and vigorously stirred. Preferably, the amount of zinc present is about 2-3 equivalents of the cyclic sulfite. The reaction is usually completed in less than 10 hours. The desired malic acid derivative can be obtained by filtration and extractive workup.

The alternative process for reduction of the β-halo malic acid derivatives by catalytic hydrogenation is performed under 15-50 psi of hydrogen pressure and at ambient temperature. Useful catalysts include palladium on carbon, Raney nickel, and the like. Effective solvents are usually aqueous-organic mixtures produced by the addition of water to the mixture resulting from the reaction of the cyclic sulfite with halide. Hydrogenation may also be carried out in the presence of an alcohol or an aromatic solvent. To ensure complete and fast reaction, a base is added to the reaction to neutralize the resulting hydrogen halide. The base is usually a metal oxide such as magnesium oxide, a hydroxide such as calcium hydroxide or potassium hydroxide, other base such as sodium acetate, or a tertiary amine such as triethylamine. The desired malic acid derivative is obtained by filtration and usual workup.

A typical workup procedure is as follows: the reaction mixture from the reduction step is filtered to remove the zinc residue or noble metal catalyst, which can be recovered. The filtrate is then acidified with dilute hydrochloric acid and extracted with an organic solvent such as ethyl acetate, ether, or methylene chloride. The combined extracts are then washed with saturated sodium chloride and sodium bicarbonate solutions and dried over anhydrous magnesium sulfate or sodium sulfate. The crude product after removal of the solvent is then purified, e.g., by distillation or chromatography on silica gel.

The overall yield of the reaction from tartrate as shown in Equation 1 is usually in the range of 65-82%. The optical purity of the malic acid derivative product is determined by $^1H$ NMR analysis of the ester produced by the reaction of the malate compound with (S)-α-methoxy-α-(trifluoromethyl)phenylacetic acid chloride. The optical purity of the malic acid derivatives typically produced in the disclosed method is substantially 100% indicating that no racemization has occurred during the various reactions and that the reactions proceed with high stereoselectivity.

Known methods can be employed to produce malic acid from the malate derivatives of the present invention. For example, malate esters can be hydrolyzed with base, e.g., aqueous alcohol sodium hydroxide under refluxing conditions. In addition, known methods can be used to produce tartaric acid derivatives from tartaric acid, with said derivatives subsequently used as starting material.

5.2. Examples

In order to more fully illustrate the nature of the invention and the manner of practicing the same, the following examples are provided, which are not to be construed as limiting the remainder of the disclosure in any way whatsoever.

5.3. General Experimental Conditions

Reactions are performed in a three-neck round-bottomed flask equipped with a reflux condenser, a thermometer and a magnetic stirring bar, either under nitrogen atmosphere or under dry air using a drying tube. Catalytic hydrogenations are performed in a Parr hydrogenation apparatus. All solvents are anhydrous or are dried before use.

Analytical thin-layer chromatography (TLC) is performed on glass silica gel plates (0.25 mm thick E. Merck silica gel 60-F254). Flash chromatography is performed on E. Merck 40–63-μm normal phase silica gel eluting with 15% to 20% or 50% ethyl acetate in hexane.

All proton NMR spectra are run on a Varian EM 360 60 MHz spectrometer using CDCl$_3$ as the solvent and tetramethylsilane as an internal standard. Optical purities of the malate products are determined by $^1$H NMR analysis of the derived esters from the reaction of the malates with (S)-α-methoxy-α-(trifluoromethyl)-phenylacetic acid on a Bruker 300 MHz spectrometer in CDCl$_3$ which in all cases showed 100% enantiomeric excess. Infrared spectra are taken on a Nicolet 5DXC FT-IR spectrometer. Optical rotations are obtained on a Perkin-Elmer 243 polarimeter.

All reagents are obtained from commercial sources and used without further purification unless otherwise stated. Zinc dust is treated briefly with 10% HCl solution and then is washed with distilled water and acetone and is dried under vacuum.

The tartrate cyclic sulfites are prepared in ≧98% yield according to the known procedure (E. Schiller, *Berichte* 1909, 42, 2017) with small modifications by reaction of tartrates with thionyl chloride without solvent or in minimum amount of solvent. From L-(+)-tartrates,(−)-tartrate cyclic sulfites are obtained. They are either used without isolation or isolated by removing the solvent and then used without further purification.

5.4. Preparation of D-(+)-diisopropyl malate

LiBr (1.3 g. 1.5 mmol) is added slowly to a cold (ice-water bath) solution of (−)-diisopropyl tartrate cyclic sulfite (2.8 g. 10 mmol) in 10 mL of DME. After addition, the mixture is heated to ca. 60°–70° C. and is stirred for 2 hrs. Thin Layer Chromatography (TLC) shows the starting cyclic sulfite is consumed. Water (10 mL) is added, followed by zinc dust (2.0 g, 30 mmol). The mixture stirs vigorously at the same temperature for 2 hrs. and is cooled. The mixture is filtered through Celite. The solid residue is washed thoroughly with water (2×10 mL) and ethyl acetate (2×10 mL). The aqueous phase is separated, acidified with conc. HCl and extracted with 3×20 mL of ethyl acetate. The combined organic phase is then washed with brine and saturated NaHCO$_3$ and is dried over MgSO$_4$. After removal of the solvent, the crude product is purified by flash chromatography on silica gel eluting with 15% EtOAc in hexane to afford 1.8 g (82%) of the title compound as a colorless liquid. $[\alpha]_{25}^{D}+12.2°$ (c 1.02, EtOH). $^1$H NMR: δ 4.9–5.4 (m, 2H), 4.5 (d,d, J=5 Hz, 6 Hz, 1H), 3.3 (d, J=5 Hz, 1H), 2.8 (d, J=6 Hz, 2 H), 1.3 (d,d, J=6 Hz, 12 H); IR (neat) 3500, 2981, 1743, 1456, 1378, 1223, 1109, 960, 826 cm$^{-1}$.

5.5. Preparation of D-(+)-diisopropyl malate

LiBr (2.6 g, 30 mmol) is added slowly to a cold (ice water bath) solution of (−)-diisopropyl tartrate cyclic sulfite (5.6 g, 20 mmol) in 20 mL of THF. After addition, the mixture is heated to ca. 60° C. and is stirred for 16 hrs. Water (20 mL) is added, followed by zinc dust (2.6 g, 40 mmol). The mixture is stirred vigorously at the same temperature for 2 hrs. and is cooled. The reaction is worked up and the product is purified as Example 5.4 to give the title compound (3.6 g, 82%). $[a]_{25}^{D}+9.6°$ (c 2.24, EtOH).

5.6. Preparation methyl 2-ethyl-3-methyl-3-hydroxypropionate

LiBr (1.3 g, 15 mmol) is added to a cold solution (icebath) of threo-methyl 2-ethyl-3-methyl-2,3-dihydroxyglycidate cyclic sulfite (2.1 g, 10 mmol) in 10 mL of DME. After addition, the mixture is heated to ca 60°–70° C. and stirred for 5 h. Water (10 mL) is added, followed by zinc dust (2.0 g, 30 mmol). The mixture is stirred vigorously at the same temperature for 2 h. The reaction is worked up as in Example 5.4 and the crude product is purified by chromatography on silica gel eluting with 25% EtOAc in hexane to give the title compound.

5.7. Preparation of D-(+)-diisopropyl malate

LiCl (1.7 g, 40 mmol) is added slowly to a solution of (−)-diisopropyl tartrate cyclic sulfite (5.6 g, 20 mmol) in 20 mL of DMF at room temperature. After addition, the mixture is heated to ca. 70° C. and is stirred for 3 hrs. TLC shows the starting cyclic sulfite is consumed. Water (20 mL) is added, followed by zinc dust (3.9 g, 60 mmol). The mixture is stirred vigorously at the same temperature for 3 hrs. and cooled. The reaction is worked up and the product is purified as Example 5.4 to afford the title compound (2.94 g, 67%). $[a]_{25}^{D}+10.6°$ (c 2.24, EtOH).

5.8. Preparation of methyl 3-hydroxy-3-isopropyl propionate

LiBr (1.3 g, 15 mmol) is added to a cold solution (icebath) of methyl 3-isopropyl 2,3-dihydroxyglycidate cyclic sulfite (2.1 g, 10 mmol) in 10 mL of DME. After addition, the mixture is heated to ca 60°–70° C. and stirred for 5 h. Water (10 mL) is added, followed by zinc dust (2.0 g, 30 mmol). The mixture is stirred vigorously at the same temperature for 2 h. The reaction is worked up as in Example 5.4 and the crude product is purified by chromatography on silica gel eluting with 25% EtOAc in hexane to give the title compound.

5.9. Preparation of D-(+)-diisopropyl malate from L-(+)-diisopropyl tartrate Thionyl Chloride (8.1 mL, 110 mmol) is added dropwise to L-(+)-diisopropyl tartrate (23.4 g, 100 mmol), followed by 10 drops of DMF. The solution is slowly heated to ca. 50° C. and is stirred while the HCl which evolves is swept away by nitrogen and is trapped with a NaOH solution. After 30 minutes, the solution is cooled and acetone (200 mL) is added. The solution is cooled to ca. 5° C. and LiBr (13 g, 150 mmol) is added in portions. During addition, the temperature rises to ca 10° C. The resulting mixture is refluxed at 50° C. for 12 hrs. The mixture cools and is transferred to a hydrogenation flask containing 10% Pd/C (3.5 g) and MgO (14 g, 350 mmol) in the presence of 150 mL of water. The mixture is hydrogenated at 25° C. under 15 psi of $H_2$ for 5.5 hrs. The mixture is filtered through Celite and the filtrate is concentrated to remove acetone and is worked up as Example 5.4 using $CH_2Cl_2$ as the extraction solvent. The crude product is distilled at 76°–80° C./0.4 mmHg to afford the title compound (17.4 g, 80%). $[a]_{25}^D + 11.6°$ (c 2.56, EtOH).

5.10. Preparation of methyl 2-methyl-3-ethyl-3-hydroxypropionate

LiBr (1.3 g, 15 mmol) is added to a cold solution (icebath) of threo-methyl 2-methyl-3-ethyl 2,3-dihydroxyglycidate cyclic sulfite (2.1 g, 10 mmol) in 10 mL of DME. After addition, the mixture is heated to ca 60°–70° C. and stirred for 5 h. Water (10 mL) is added, followed by zinc dust (2.0 g, 30 mmol). The mixture is stirred vigorously at the same temperature for 2 h. The reaction is worked up as in Example 5.4 and the crude product is purified by chromatography on silica gel eluting with 25% EtOAc in hexane to give the title compound.

5.11. Preparation of D-(+)-diethyl malate

LiBr (13 g, 150 mmol) is added slowly to a cold (icewater bath) solution of (-)-diethyl tartrate cyclic sulfite (25.2 g, 100 mmol) in 100 mL of DME. After addition, the mixture is heated to ca. 80° C. and is stirred for 2 hrs. TLC shows the starting cyclic sulfite is consumed. Water (100 mL) is added, followed by zinc dust (20 g, 300 mmol). The mixture is stirred vigorously at the same temperature for 1 hr. and cooled. The reaction is worked up as Example 5.4 and the product is purified by distillation at 86°–90° C./1.4 mm Hg to give the title compound as a colorless liquid (15.7 g, 82%). $[a]_{25}^D + 10.7°$ (c 2.29, EtOH). $^1$H NMR: δ 4.5 (d,d, J=5 Hz, 7 Hz, 1 H), 4.0–4.6 (m, 4 H), 3.3 (d, J=5 Hz, 1 H), 2.8 (d, J=Hz, 2 H), 1.3 (dt, J=7 Hz, 6 H); IR (neat) 3500, 1994, 1743, 1378, 1230, 1103, 1032, 857 cm$^{-1}$.

5.12. preparation of D-(+)-N,N,N',N'-tetraethyl malamide from L-(+)-N,N,N', N'-tetraethyl tartramide Thionyl chloride (8.1 mL, 110 mmol) is added dropwise to L-(+)-N,N,N',N'-tetraethyl tartramide (26.0 g, 100 mmol) in ca. 30 mL of DME. The mixture is slowly heated to ca. 50°–60° C. and stirred while the evolved HCl gas is swept away by nitrogen. After all the tartramide is consumed, the mixture is cooled to ambient temperature and DME (170 mL) is added. The solution is cooled to ca. 5° C. and LiBr (13 g, 150 mmol) is added in portions. The resulting mixture is then heated at 60°–70° C. for 12 h. Zinc dust (16.4 g, 250 mmol) is added followed by ca. 1 mL of water. The mixture is stirred at the same temperature for 2 h. The reaction is then worked up as Example 5.4 and the crude product is distilled to give the title compound.

5.13. Preparation of D-(+)-diethyl malate from L-(+)-diethyl tartrate

Thionyl Chloride (8.1 mL, 110 mmol) is added dropwise to L-(+)-diethyl tartrate (20.6 g, 100 mmol), followed by 10 drops of DMF. The solution is slowly heated to ca. 50° C. and stirred while the HCl which evolves is swept away by nitrogen and is trapped with a NaOH solution. After one hour, the solution cools and acetone (100 mL) is added. The solution is cooled to ca. 0° C. and LiBr (17.4 g, 200 mmol) is added in portions. During addition, the temperature raised to ca. 10° C. The resulting mixture is refluxed at 45°–50° C. for 7 hrs. Zinc (16.4 g, 250 mmol) is added, followed by 0.5 mL of water. The mixture is stirred at the same temperature for 2 hrs. The reaction is worked up as Example 5.4 and the crude product is distilled to give the title compound (13.3 g, 70%). $[a]_{25}^D + 10.5°$ (c 2.05, EtOH).

5.14. Preparation of D-(+)-diethyl malate

LiBr (2.6 g, 30 mmol) is added slowly to a cold (ice water bath) solution of (−)-diethyl tartrate cyclic sulfite (5.1 g, 20 mmol) in 20 mL of DME. After addition, the mixture is heated to ca. 50° C. and stirred for 5 hrs. TLC showed the starting cyclic sulfite is consumed. The mixture is cooled and transferred with the aid of 20 mL of DME to a hydrogenation flask containing 10% Pd/C (1.5 g) and MgO (2.4 g, 60 mmol) in 100 mL of water. The mixture is hydrogenated at 25° C. under 50 psi of $H_2$ pressure for 30 minutes. The mixture is filtered and worked up as Example 5.9. The crude product is purified by flash chromatography eluting with 15% EtOAc in hexane to provide the title compound (2.45 g, 64%). $[a]_{25}^D + 10.3°$ (c 2 23, EtOH).

5.15. Preparation of D-(+)-diphenyl malate from L-(+)-diphenyl tartrate

Thionyl chloride (8.1 mL, 110 mmol) is added dropwise to L-(+)-diphenyl tartrate (30.2 g, 100 mmol) in ca. 30 mL of EtOAc. The mixture is slowly heated to ca. 50°–60° C. and stirred while the evolved HCl gas is swept away by nitrogen. After all the tartrate is consumed, the mixture is cooled to ca. 5° C. and LiBr (13.0 g, 50 mmol) is added in portion. The resulting mixture is then refluxed for 12 h. The mixture is cooled to ambient temperature and transferred to a hydrogenation flask containing 10% Pd on carbon (3.5 g) and MgO (14 g, 350 mmol) in the presence of 150 mL of water. The mixture is hydrogenated at ambient temperature under 15–50 psi of hydrogen until completion. The mixture is then filtered and worked up as Example 5.9. The crude product can be purified by chromatography on silica gel eluting with 25% EtOAc in hexane to give the title compound.

5 16 preparation of D-(+)-diethyl malate

LiBr (2.6 g, 30 mmol) is added slowly to a cold (ice water bath) solution of (−)-diethyl tartrate cyclic sulfite (5.1 g, 20 mmol) in 20 mL of DME. After addition the mixture is heated to ca. 70° C. and stirred for 12 hrs. TLC showed the staring cyclic sulfite is consumed. The mixture is cooled and transferred to a hydrogenation flask containing active Raney nickel (10 g, 50% slurry in water, pH>9) in 150 mL of MeOH. The mixture is hydrogenated at 25° C. under 50 psi of $H_2$ pressure for 5 hrs. The mixture is filtered, the filtrate is concentrated and worked up as Example 5.9. The crude product is purified by flash chromatography eluting with 15% and 20% EtOAc in hexane to provide the title compound (2.67 g, 70%). $[a]_{25}^D + 9.9°$ (c 2.22, EtOH).

5.17. Preparation of D-(+)-diethyl malate

LiBr (2.6 g, 30 mmol) is added slowly to a solution of (−)-diethyl tartrate cyclic sulfite (5.1 g, 20 mmol) in 20 mL of acetone at 0° C. During addition, the temperature is warmed up to 10° C. After addition, the mixture is refluxed at ca. 50° C. and stirred for 6 hrs. TLC showed the starting cyclic sulfite is consumed. The mixture is cooled and transferred to a hydrogenation flask containing 10% Pd/C (1.0 g) and MgO (2.4 g, 60 mmol) in 100 mL of water. The mixture is hydrogenated at 25° C. under 15–40 psi of $H_2$ pressure for 2 hrs. The mixture is filtered and worked up as Example 5.9. The crude product is purified by flash chromatography eluting with 15% and 20% EtOAc in hexane to provide the title compound (2.83 g, 74%). $[a]_{25}^D +10.6$ (c 2.22, EtOH).

5.18. Preparation of D-(+)-dimethyl malate from L-(+)-dimethyl tartrate

Thionyl chloride (8.1 mL, 110 mmol) is added dropwise to a suspension of L-(+)-dimethyl tartrate (17.8 g, 100 mmol) in 25 mL of EtOAc. The mixture is heated at 60° C. for 15 hrs. The resulting solution is diluted with 100 mL of DME and then is cooled to 0° C. LiBr (17.4 g, 200 mmol) is added in portions. The resulting mixture is heated at 70° C. and stirred for 2 hrs. Zinc dust (16.4 g, 250 mmol) is added and the mixture is refluxed at 80° C. for 5 hrs. The mixture is cooled and worked up as Example 5.4. Because the product is water soluble, low recovery results. The crude product is purified by chromatography diluting with 20% and 50% EtOAc in hexane to give the title compound as a colorless liquid (6.17 g, 38%). $[a]_{25}^D +9.1°$ (c 2.15, EtOH). $^1H$ NMR: δ 4.5 (t, J=6 Hz, 1 H), 3.85 (s, 3 H), 3.75 (s, 3 H), 3.5 (bs, 1 H), 2.8 (d, J=6 Hz, 2 H); IR (neat) 3494, 3008, 2959, 1743, 1440, 1370, 1279, 1222, 1173, 1110, 1046, 1004, 850 $cm^{-1}$.

5.19. Preparation of D-(+)-diisopropyl malate $CaCl_2$ (2.22 g, 20 mmol) is added to a solution of (−)-diisopropyl tartrate cyclic sulfite (2.8 g, 10 mmol) in 10 mL of DMF. After addition, the mixture is heated to ca 60° C. and stirred for 16 h. Water (10 mL) is added, followed by zinc dust (2.0 g, 30 mmol). The mixture is stirred vigorously at 70° C. for 5 h. The reaction is worked up as in Example 5.4 and the crude product is purified by chromatography on silica gel eluting with 25% EtOAc in hexane to give the title compound as a colorless oil (0.86 g, 40% yield).

The preceding examples are given as an illustration of specific embodiments of the present invention. These examples are, thus, not to be construed as limiting the scope of the invention in any way. Indeed, other embodiments of the present invention are readily apparent to those of ordinary skill from a reading of the present disclosure. These embodiments are considered to fall within the scope and spirit of the present invention, boundaries of which are defined solely by the following claims.

I claim:

1. A method of transforming a tartaric acid derivative having no free acid or thioacid groups to a malic acid derivative having no free acid or thioacid groups, comprising:
   (a) allowing a derivative of tartaric acid having no free acid or thioacid groups to react with a thionyl halide to form a cyclic tartrate sulfite;
   (b) allowing said cyclic tartrate sulfite to react with an organic or inorganic halide salt to form a β-halo malic acid sulfite; and
   (c) allowing said β-halo malic acid sulfite to react with a reducing agent to provide a derivative of malic acid having no free acid or thioacid groups.

2. The method of claim 1 in which the tartaric acid derivative is the L-isomer thereof and the malic acid derivative is the D-isomer thereof.

3. The method of claim 2 in which the malic acid derivative is an ester of D-malic acid.

4. The method of claim 1 which further comprises transforming the derivative of malic acid to free malic acid or a salt thereof.

5. The method of claim 4 in which the free malic acid or salt thereof is the D-isomer thereof.

* * * * *